US012605526B2

(12) United States Patent
Schabert et al.

(10) Patent No.: US 12,605,526 B2
(45) Date of Patent: Apr. 21, 2026

(54) INTRAVASCULAR MEDICAL DEVICES INCLUDING LASER CUT TUBE

(71) Applicant: Deepin Technologies, LLC, San Jose, CA (US)

(72) Inventors: Jon Schabert, San Jose, CA (US); Jiaxu Wang, San Jose, CA (US); Alex Kubacki, San Jose, CA (US); Alan Thomas, San Francisco, CA (US)

(73) Assignee: Deepin Technologies, LLC, San Jose, CA (US)

( * ) Notice: Subject to any disclaimer, the term of this patent is extended or adjusted under 35 U.S.C. 154(b) by 0 days.

(21) Appl. No.: 19/315,518

(22) Filed: Aug. 30, 2025

(65) Prior Publication Data

US 2025/0381367 A1     Dec. 18, 2025

Related U.S. Application Data

(63) Continuation of application No. 19/043,429, filed on Feb. 1, 2025.

(60) Provisional application No. 63/554,136, filed on Feb. 15, 2024.

(51) Int. Cl.
*A61M 25/01* (2006.01)
*A61M 25/00* (2006.01)
*A61M 25/09* (2006.01)

(52) U.S. Cl.
CPC .... *A61M 25/0138* (2013.01); *A61M 25/0013* (2013.01); *A61M 2025/09083* (2013.01); *A61M 2210/12* (2013.01)

(58) Field of Classification Search
CPC .......... A61M 25/0138; A61M 25/0013; A61M 2025/09083
See application file for complete search history.

(56) References Cited

U.S. PATENT DOCUMENTS

| | | |
|---|---|---|
| 1,065,018 A | 6/1913 | Barber |
| 5,911,717 A | 6/1999 | Jacobsen |
| 6,014,919 A | 1/2000 | Jacobsen |
| 6,017,319 A | 1/2000 | Jacobsen |
| 6,022,369 A | 2/2000 | Jacobsen |
| 6,063,101 A | 5/2000 | Jacobsen |
| 6,183,410 B1 | 2/2001 | Jacobsen |
| 6,214,042 B1 | 4/2001 | Jacobsen |
| 6,302,870 B1 | 10/2001 | Jacobsen |
| 6,428,489 B1 | 8/2002 | Jacobsen |

(Continued)

OTHER PUBLICATIONS

SIPO of China, Office Action in Chinese Application No. 202510164537.X, Aug. 27, 2025, 27 pages.

*Primary Examiner* — Dung T Ulsh
(74) *Attorney, Agent, or Firm* — Deepin IP

(57) ABSTRACT

An intravascular device includes a tube member. The tube member comprises a distal portion and a proximal portion. Each of the distal portion and the proximal portion of the tube member comprises a plurality of cuts circumferentially extending around a longitudinal axis of the tube member. The plurality of cuts of the distal portion of the tube member comprises a first pitch, a first cut length, and a first uncut length, the plurality of cuts of the proximal portion of the tube member comprises a second pitch, a second cut length, and a second uncut length, and the first pitch is less than the second pitch, the first cut length is greater than the second length, and the first uncut length is less than the second uncut length.

16 Claims, 11 Drawing Sheets

(56)                    References Cited

U.S. PATENT DOCUMENTS

| | | | |
|---|---|---|---|
| 6,440,088 B1 | 8/2002 | Jacobsen | |
| 6,478,778 B1 | 11/2002 | Jacobsen | |
| 7,833,564 B2 | 11/2010 | Chen | |
| 7,878,984 B2 | 2/2011 | Jacobsen | |
| 7,914,466 B2 | 3/2011 | Davis | |
| 7,914,467 B2 | 3/2011 | Layman | |
| 8,048,004 B2 | 11/2011 | Davis | |
| 8,257,279 B2 | 9/2012 | Davis | |
| 8,376,961 B2 | 2/2013 | Layman | |
| 8,419,658 B2 | 4/2013 | Eskuri | |
| 8,460,213 B2 | 6/2013 | Northrop | |
| 8,551,021 B2 | 10/2013 | Voeller | |
| 8,556,914 B2 | 10/2013 | Vrba | |
| 8,784,337 B2 | 7/2014 | Voeller | |
| 8,795,202 B2 | 8/2014 | Northrop | |
| 8,870,790 B2 | 10/2014 | Davis | |
| 8,900,163 B2 | 12/2014 | Jacobsen | |
| 8,915,865 B2 | 12/2014 | Jacobsen | |
| 8,932,235 B2 | 1/2015 | Jacobsen | |
| 8,936,558 B2 | 1/2015 | Jacobsen | |
| 8,939,916 B2 | 1/2015 | Jacobsen | |
| 9,067,332 B2 | 6/2015 | Lippert | |
| 9,067,333 B2 | 6/2015 | Lippert | |
| 9,072,873 B2 | 7/2015 | Lippert | |
| 9,072,874 B2 | 7/2015 | Northrop | |
| 9,227,037 B2 | 1/2016 | Northrop | |
| 9,375,234 B2 | 6/2016 | Vrba | |
| 9,616,195 B2 | 4/2017 | Lippert | |
| 9,636,115 B2 | 5/2017 | Henry | |
| 9,662,798 B2 | 5/2017 | Christian | |
| 9,950,137 B2 | 4/2018 | Lippert | |
| 10,232,141 B2 | 3/2019 | Christian | |
| 10,315,007 B2 | 6/2019 | Chan | |
| 10,363,389 B2 | 7/2019 | Lippert | |
| 10,722,690 B2 | 7/2020 | McGowan | |
| 10,821,268 B2 | 11/2020 | Snyder | |
| 10,953,202 B2 | 3/2021 | Lippert | |
| 10,953,203 B2 | 3/2021 | Lippert | |
| 10,980,968 B2 | 4/2021 | Christian | |
| 11,052,228 B2 | 7/2021 | Lippert | |
| 11,207,502 B2 | 12/2021 | Lippert | |
| 11,253,277 B2 | 2/2022 | Buck | |
| 11,259,821 B2 | 3/2022 | Buck | |
| 11,369,351 B2 | 6/2022 | Davis | |
| 11,406,791 B2 | 8/2022 | Lippert | |
| 11,420,022 B2 | 8/2022 | Northrop | |
| 11,439,799 B2 | 9/2022 | Buck | |
| 11,452,541 B2 | 9/2022 | Lippert | |
| 11,457,936 B2 | 10/2022 | Buck | |
| 11,819,228 B2 | 11/2023 | Buck | |
| 11,890,434 B2 | 2/2024 | Lippert | |
| 11,896,781 B2 | 2/2024 | Northrop | |
| 11,951,267 B2 | 4/2024 | Lippert | |
| 12,011,555 B2 | 6/2024 | Davis | |
| 12,115,324 B2 | 10/2024 | Lippert | |
| 12,178,975 B2 | 12/2024 | Lippert | |
| 12,220,538 B2 | 2/2025 | Lippert | |
| 2002/0082499 A1 | 6/2002 | Jacobsen | |
| 2003/0009208 A1 | 1/2003 | Snyder | |
| 2004/0111044 A1 | 6/2004 | Davis | |
| 2004/0181174 A2 | 9/2004 | Davis | |
| 2007/0287955 A1 | 12/2007 | Layman | |
| 2008/0021347 A1 | 1/2008 | Jacobsen | |
| 2008/0021348 A1 | 1/2008 | Jacobsen | |
| 2008/0021400 A1 | 1/2008 | Jacobsen | |
| 2008/0021401 A1 | 1/2008 | Jacobsen | |
| 2008/0021402 A1 | 1/2008 | Jacobsen | |
| 2008/0021403 A1 | 1/2008 | Jacobsen | |
| 2008/0021404 A1 | 1/2008 | Jacobsen | |
| 2008/0021405 A1 | 1/2008 | Jacobsen | |
| 2008/0021406 A1 | 1/2008 | Jacobsen | |
| 2008/0021407 A1 | 1/2008 | Jacobsen | |
| 2008/0021408 A1 | 1/2008 | Jacobsen | |
| 2008/0077119 A1 | 3/2008 | Snyder | |
| 2008/0097247 A1 | 4/2008 | Eskuri | |
| 2008/0125753 A1 | 5/2008 | Chen | |
| 2008/0147170 A1 | 6/2008 | Vrba | |
| 2008/0262474 A1 | 10/2008 | Northrop | |
| 2009/0036832 A1 | 2/2009 | Skujins | |
| 2009/0177119 A1 | 7/2009 | Heidner | |
| 2009/0177185 A1 | 7/2009 | Northrop | |
| 2009/0254000 A1 | 10/2009 | Layman | |
| 2010/0063479 A1 | 3/2010 | Merdan | |
| 2010/0145308 A1 | 6/2010 | Layman | |
| 2010/0256527 A1 | 10/2010 | Lippert | |
| 2010/0256528 A1 | 10/2010 | Lippert | |
| 2010/0256601 A1 | 10/2010 | Lippert | |
| 2010/0256602 A1 | 10/2010 | Lippert | |
| 2010/0256603 A1 | 10/2010 | Lippert | |
| 2010/0256604 A1 | 10/2010 | Lippert | |
| 2010/0256605 A1 | 10/2010 | Lippert | |
| 2010/0256606 A1 | 10/2010 | Lippert | |
| 2011/0245808 A1* | 10/2011 | Voeller | A61M 25/0054 |
| | | | 604/528 |
| 2012/0203207 A1 | 8/2012 | Northrop | |
| 2012/0289938 A1 | 11/2012 | Northrop | |
| 2013/0267913 A1 | 10/2013 | Northrop | |
| 2014/0039532 A1 | 2/2014 | Vrba | |
| 2014/0052107 A1 | 2/2014 | Voeller | |
| 2014/0336620 A1 | 11/2014 | Layman | |
| 2016/0015935 A1 | 1/2016 | Chan | |
| 2017/0182295 A1 | 6/2017 | McGowan | |
| 2017/0189643 A1 | 7/2017 | Christian | |
| 2018/0015261 A1 | 1/2018 | Lippert | |
| 2018/0015262 A1 | 1/2018 | Lippert | |
| 2018/0015263 A1 | 1/2018 | Lippert | |
| 2018/0071496 A1 | 3/2018 | Snyder | |
| 2018/0177517 A1 | 6/2018 | Lippert | |
| 2018/0193607 A1 | 7/2018 | Lippert | |
| 2019/0105463 A1 | 4/2019 | Christian | |
| 2019/0184143 A1 | 6/2019 | Onushko | |
| 2019/0262598 A1 | 8/2019 | Mock | |
| 2019/0290883 A1 | 9/2019 | Lippert | |
| 2020/0094027 A1 | 3/2020 | Davis | |
| 2020/0121308 A1 | 4/2020 | Davis | |
| 2020/0222672 A1 | 7/2020 | Davis | |
| 2020/0345975 A1 | 11/2020 | Snyder | |
| 2021/0008351 A1 | 1/2021 | Snyder | |
| 2021/0128885 A1 | 5/2021 | Lu | |
| 2021/0162184 A1 | 6/2021 | Lippert | |
| 2021/0178127 A1 | 6/2021 | Gerberding | |
| 2021/0178128 A1 | 6/2021 | Lippert | |
| 2021/0186536 A1 | 6/2021 | Buck | |
| 2021/0186537 A1 | 6/2021 | Buck | |
| 2021/0186542 A1 | 6/2021 | Buck | |
| 2021/0187244 A1 | 6/2021 | Buck | |
| 2021/0213241 A1 | 7/2021 | Christian | |
| 2021/0228845 A1 | 7/2021 | Lippert | |
| 2021/0275779 A1 | 9/2021 | Northrop | |
| 2021/0282759 A1 | 9/2021 | Layman | |
| 2021/0283372 A1 | 9/2021 | Murphy | |
| 2021/0283380 A1 | 9/2021 | Lippert | |
| 2021/0315596 A1 | 10/2021 | Buck | |
| 2021/0315597 A1 | 10/2021 | Buck | |
| 2021/0315598 A1 | 10/2021 | Buck | |
| 2021/0316121 A1 | 10/2021 | Buck | |
| 2021/0316127 A1 | 10/2021 | Buck | |
| 2021/0346656 A1 | 11/2021 | Lippert | |
| 2022/0105312 A1 | 4/2022 | Davis | |
| 2022/0105318 A1 | 4/2022 | Davis | |
| 2022/0280147 A1 | 9/2022 | Davis | |
| 2022/0296850 A1 | 9/2022 | Lippert | |
| 2022/0378459 A1 | 12/2022 | Lippert | |
| 2022/0401699 A1 | 12/2022 | Northrop | |
| 2023/0015259 A1 | 1/2023 | Buck | |
| 2023/0046468 A1 | 2/2023 | Lau | |
| 2023/0047098 A1 | 2/2023 | Lau | |
| 2023/0048055 A1 | 2/2023 | Lau | |
| 2023/0048388 A1 | 2/2023 | Lau | |
| 2023/0052862 A1 | 2/2023 | Lau | |
| 2023/0082226 A1 | 3/2023 | Lippert | |
| 2024/0032949 A1 | 2/2024 | Yang | |
| 2024/0033019 A1 | 2/2024 | Lau | |
| 2024/0033486 A1 | 2/2024 | Lau | |

(56)                    References Cited

U.S. PATENT DOCUMENTS

| | | | |
|---|---|---|---|
| 2024/0123196 | A1 | 4/2024 | Lippert |
| 2024/0181207 | A1 | 6/2024 | Bartholomew |
| 2024/0181208 | A1 | 6/2024 | Bartholomew |
| 2024/0181209 | A1 | 6/2024 | Bartholomew |
| 2024/0181224 | A1 | 6/2024 | Bartholomew |
| 2024/0183382 | A1 | 6/2024 | Bartholomew |
| 2024/0198059 | A1 | 6/2024 | Lippert |
| 2024/0207570 | A1 | 6/2024 | Mar |
| 2024/0207577 | A1 | 6/2024 | Pope |
| 2024/0216653 | A1 | 7/2024 | Pope |
| 2024/0299710 | A1 | 9/2024 | Davis |
| 2024/0342444 | A1 | 10/2024 | Lippert |
| 2024/0390639 | A1 | 11/2024 | Lesueur |

* cited by examiner

312

312

312

315

1200

1202
PROVIDING AN ELONGATE POLYMER LINER

1204
PROVIDING A TUBE MEMBER

1206
FORMING A PLURALITY OF CUTS IN THE TUBE
MEMBER

1208
COUPLING THE TUBE MEMBER TO THE
ELONGATE ELONGATE POLYMER LINER

1210
APPLYING A JACKET LAYER

INTRAVASCULAR MEDICAL DEVICES INCLUDING LASER CUT TUBE

CROSS-REFERENCE TO RELATED APPLICATIONS

This application is a continuation of U.S. application Ser. No. 19/043,429 filed Feb. 1, 2025, entitled "Intravascular Medical Devices Including Laser Cut Tube," which claims priority to U.S. provisional patent application No. 63/554,136 filed Feb. 15, 2024 entitled "Intravascular Medical Devices Including Laser Cut Tube," the disclosure of which is hereby incorporated by reference in its entirety.

TECHNICAL FIELD

This application relates generally to medical devices and methods of making and using medical devices to treat diseases. Particularly, various embodiments of an intravascular device and a method of making the same are described.

BACKGROUND

Intravascular devices such as catheters and guidewires are widely used in medical procedures for diagnosis and treatment. Such devices often require a variable stiffness profile, typically with the most flexible section at the distal end while maintaining good torque transmission for trackability and delivery in tortuous anatomy.

For example, a catheter typically includes a polymer inner liner, a metal reinforcement layer, and a polymer outer jacket layer. The metal reinforcement layer is the primary contributor to the catheter's stiffness and torque transmission. Traditionally, metal coils or braids are used as catheter reinforcement layers. As micro-machining technology has evolved, micro-machined hypotubes have also entered the field as device components. However, micro-machining techniques are limited in processing speed and cut geometry and cuttable parameters they can impart on the hypotube due to the size and shape of the cutting element used.

Therefore, while advancement has been made in the field of intravascular devices, there is still a general need for improvement to overcome these and other problems experienced by the conventional techniques. It would be desirable to provide a new technique for achieving cut parameters and geometries on an intravascular device that can balance the complex bending flexibility, tensile strength, and torque transmission requirements for various medical applications.

SUMMARY

In one aspect, embodiments of the disclosure feature an intravascular device. In general, an embodiment of the intravascular device comprises a tube member comprising a distal portion and a proximal portion. Each of the distal portion and the proximal portion of the tube member comprises a plurality of cuts circumferentially extending around a longitudinal axis of the tube member. The plurality of cuts of the distal portion of the tube member comprises a first pitch, a first cut length, and a first uncut length, the plurality of cuts of the proximal portion of the tube member comprises a second pitch, a second cut length, and a second uncut length, and the first pitch is less than the second pitch, the first cut length is greater than the second length, and the first uncut length is less than the second uncut length.

In various embodiments of the aspect, the plurality of cuts of the distal portion comprises a first cut width, and the plurality of cuts of the proximal portion comprises a second cut width less than the first cut width.

In various embodiments of the aspect, each of the first pitch, the first cut length, the first uncut length, and the first cut width comprises a constant value. In various embodiments of the aspect, each of the first pitch, the first cut length, the first uncut length, and the first cut width varies linearly along the distal portion or comprises an instantaneous change.

In various embodiments of the aspect, each of the second pitch, the second cut length, the second uncut length, and the second cut width comprises a constant value. In various embodiments of the aspect, each of the second pitch, the second cut length, the second uncut length, and the second cut width varies linearly along the proximal portion or comprises an instantaneous change.

In various embodiments of the aspect, the combination of the first cut length and the first uncut length is greater than or equal to the combination of the second cut length and the second uncut length.

In various embodiments of the aspect, the plurality of cuts of the distal portion are vertical cuts, and the plurality of cuts of the proximal portion are vertical cuts.

In various embodiments of the aspect, the plurality of cuts of the distal portion are vertical cuts, and the plurality of cuts of the proximal portion are helical cuts.

In various embodiments of the aspect, the plurality of cuts of the distal portion are helical cuts, and the plurality of cuts of the proximal portion are helical cuts.

In various embodiments of the aspect, the tube member further comprises a transition portion between the distal portion and the proximal portion. The transition portion of the tube member comprises a plurality of cuts circumferentially extending around the longitudinal axis of the tube member. The plurality of cuts of the transition portion are helical cuts and comprises a third pitch, a third cut length, and a third uncut length. In an embodiment, the third pitch of the plurality of cuts of the transition portion increases in a proximal direction. The third pitch can increase linearly or non-linearly e.g., including instantaneous changes. In an embodiment, the third cut length and the third uncut length of the transition portion are constant. In an embodiment, the third cut length decreases in the proximal direction, and the third uncut length increases in the proximal direction. The third cut length and the third uncut length may also be varied linearly or non-linearly, which includes instantaneous changes. In an embodiment, the plurality of cuts of the transition portion comprises a third cut width less than or equal to the first cut width of the plurality cuts of the distal portion. In an embodiment, the third pitch is constant, the third cut length decreases in a proximal direction, and the third uncut length increases in the proximal direction. In an embodiment, each of the third pitch, the third cut length, and the third uncut length of the transition portion is constant.

In various embodiments of the aspect, the tube member further comprises a transition portion between the distal portion and the proximal portion. The transition portion of the tube member comprises a plurality of cuts circumferentially extending around the longitudinal axis of the tube member. The plurality of cuts of the transition portion are vertical cuts, and comprises a third pitch increasing in the proximal direction, a third cut length decreasing in a proximal direction, and a third uncut length increasing in the proximal direction.

In various embodiments of the aspect, the distal portion of the tube member extends a length of 10 cm or less from a distal end extremity of the tube member, and the proximal portion of the tube member extends from a location at 15 cm or more from the distal end extremity. In an embodiment, the first pitch of the plurality of cuts of the distal portion is in a range between 0.03 mm and 0.30 mm, and the second pitch of the plurality of cuts of the proximal portion is in a range between 0.10 mm and 1.00 mm. In an embodiment, the plurality of cuts of the distal portion comprises a first cut width in a range between 0.020 mm and 0.160 mm, and the plurality of cuts of the proximal portion comprises a second cut width in a range between 0.020 mm and 0.051 mm. In an embodiment, the first cut length of the plurality of cuts of the distal portion is in a range between 60 degrees and 177 degrees, the first uncut length of the plurality of cuts of the distal portion is in a range between 3 degrees and 15 degrees, the second cut length of the plurality of cuts of the proximal portion is in a range between 60 degrees and 165 degrees, and the second uncut length of the plurality of cuts of the proximal portion is in a range between 15 degrees and 40 degrees. In an embodiment, a combination of the first cut length and the first uncut length is between 75 and 180 degrees, and a combination of the second cut length and second uncut length is between 75 and 180 degrees.

In various embodiments of the aspect, the intravascular device comprises a catheter including an elongate inner liner having a lumen and a tube member described above encompassing at least a distal portion of the elongate inner liner.

In various embodiments of the aspect, the intravascular device comprises a guidewire including an elongate core wire and a tube member described above encompassing at least a distal portion of the elongate core wire.

In another aspect, embodiments of the disclosure feature a tube member for use in a medical device. The tube member comprises a distal portion and a proximal portion. Each of the distal portion and the proximal portion of the tube member comprises a plurality of cuts circumferentially extending around a longitudinal axis of the tube member. The plurality of cuts of the distal portion of the tube member comprises a first pitch, a first cut length, and a first uncut length, the plurality of cuts of the proximal portion of the tube member comprises a second pitch, a second cut length, and a second uncut length, and the first pitch is less than the second pitch, the first cut length is greater than the second length, and the first uncut length is less than the second uncut length.

In various embodiments of the aspect, the plurality of cuts of the distal portion comprises a first cut width, and the plurality of cuts of the proximal portion comprises a second cut width less than the first cut width.

In various embodiments of the aspect, each of the first pitch, the first cut length, the first uncut length, and the first cut width comprises a constant value. In various embodiments of the aspect, each of the first pitch, the first cut length, the first uncut length, and the first cut width varies linearly along the distal portion or comprises an instantaneous change.

In various embodiments of the aspect, each of the second pitch, the second cut length, the second uncut length, and the second cut width comprises a constant value. In various embodiments of the aspect, each of the second pitch, the second cut length, the second uncut length, and the second cut width varies linearly along the proximal portion or comprises an instantaneous change.

In various embodiments of the aspect, the combination of the first cut length and the first uncut length is greater than or equal to the combination of the second cut length and the second uncut length.

In various embodiments of the aspect, the plurality of cuts of the distal portion are vertical cuts, and the plurality of cuts of the proximal portion are vertical cuts.

In various embodiments of the aspect, the plurality of cuts of the distal portion are vertical cuts, and the plurality of cuts of the proximal portion are helical cuts.

In various embodiments of the aspect, the plurality of cuts of the distal portion are helical cuts, and the plurality of cuts of the proximal portion are helical cuts.

In various embodiments of the aspect, the tube member further comprises a transition portion between the distal portion and the proximal portion. The transition portion of the tube member comprises a plurality of cuts circumferentially extending around the longitudinal axis of the tube member. The plurality of cuts of the transition portion are helical cuts and comprises a third pitch, a third cut length, and a third uncut length. In an embodiment, the third pitch of the plurality of cuts of the transition portion increases in a proximal direction. The third pitch can increase linearly or non-linearly. In an embodiment, the third cut length and the third uncut length of the transition portion are constant. In an embodiment, the third cut length decreases in the proximal direction, and the third uncut length increases in the proximal direction. The third cut length and the third uncut length may also be varied linearly or non-linearly, which includes instantaneous changes. In an embodiment, the plurality of cuts of the transition portion comprises a third cut width less than or equal to the first cut width of the plurality cuts of the distal portion. In an embodiment, the third pitch is constant, the third cut length decreases in a proximal direction, and the third uncut length increases in the proximal direction. In an embodiment, each of the third pitch, the third cut length, and the third uncut length of the transition portion is constant.

In various embodiments of the aspect, the tube member further comprises a transition portion between the distal portion and the proximal portion. The transition portion of the tube member comprises a plurality of cuts circumferentially extending around the longitudinal axis of the tube member. The plurality of cuts of the transition portion are vertical cuts, and comprises a third pitch increasing in the proximal direction, a third cut length decreasing in a proximal direction, and a third uncut length increasing in the proximal direction.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a summary of certain forms the invention might take and are not intended to limit the scope of the invention. Other aspects and embodiments of the disclosure are described in the section of Detailed Description.

These and various other aspects, embodiments, features, and advantages of the disclosure will become better understood upon reading of the following detailed description in conjunction with the accompanying drawings.

DETAILED DESCRIPTION OF EMBODIMENTS

With reference to the figures, various embodiments of an intravascular device and a method of making intravascular devices will now be described. The figures are intended to facilitate description of embodiments of the disclosure and are not necessarily drawn to scale. Certain specific details may be set forth in the figures to provide a thorough understanding of the disclosure. It will be apparent to one of ordinary skill in the art that some of these specific details may not be employed to practice embodiments of the disclosure. In other instances, structures, components, systems, materials, and/or operations often associated with known medical procedures may not be shown or described in detail to avoid unnecessarily obscuring description of embodiments of the disclosure.

Embodiments of the disclosure provide an intravascular device comprising a tube member for reinforcement and improvement of performance of the intravascular device. The tube member includes a plurality of cuts with a unique cut pattern and/or parameters such as pitch, cut width, cut length, and uncut length etc. that can desirably balance the bending flexibility, torsional rigidity, and tensile strength of the intravascular device. Embodiments of the disclosure also provide a method of making intravascular devices using laser to achieve a new cut geometry and pattern unattainable by conventional techniques.

Figure 1:
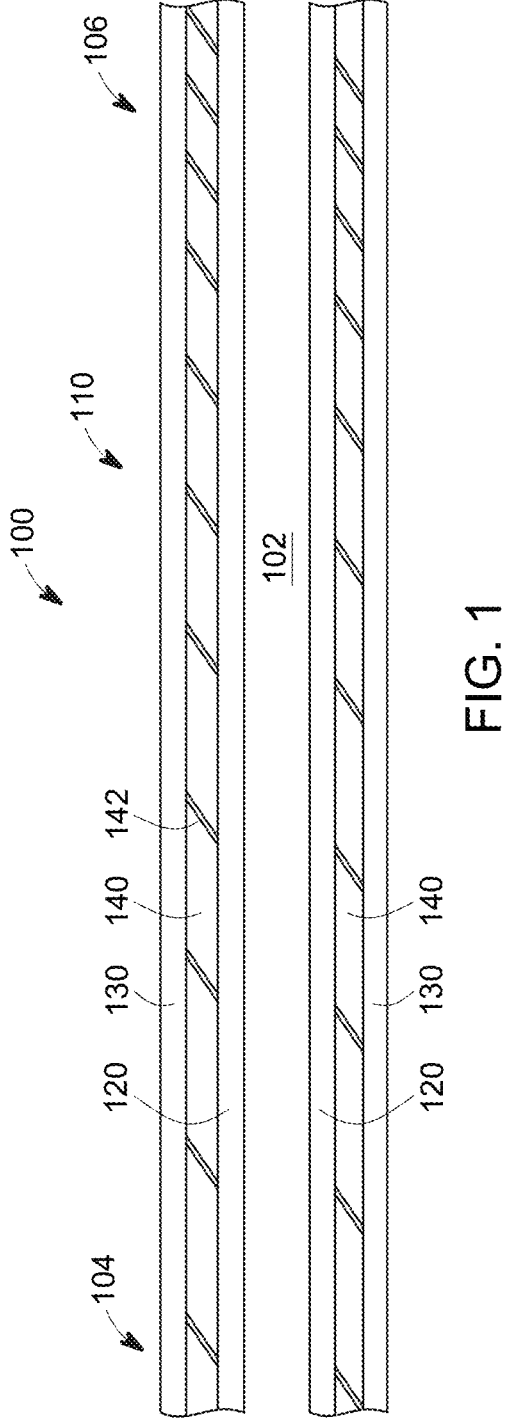
FIG. 1 is a simplified illustration of a segment or portion of an example tubular intravascular device according to embodiments of the disclosure.

FIG. 1 illustrates an example intravascular device 100 in a cross-sectional view according to embodiments of the disclosure. The intravascular device 100 can be configured for use to perform medical procedures such as neuro-, cardio-, or peripheral vasculature intervention. In a broad overview, the example intravascular device 100 comprises an elongate body 110 having a lumen 102 extending from a proximal end 104 to a distal end 106. The elongate body 110 may include an inner liner 120, an outer layer 130, and a tube member 140 between the inner liner 120 and the outer layer 130. The inner liner 120 may extend through the entire length of the elongate body 110 defining the lumen 102 of the intravascular device 100. The inner liner 120 can be constructed from a lubricious or low-friction material to provide a smooth surface for advancement of devices or objects through the inner lumen 102. Suitable lubricious materials include but are not limited to polytetrafluoroethylene (PTFE), fluorinated ethylene propylene (FEP), siloxane, and other suitable polymeric materials. The polymeric materials may include additives such as siloxane. The outer layer 130 may include a jacket or sheath to provide mechanical integrity for the intravascular device 100. The outer layer 130 may be constructed from a material such as a thermoplastic elastomer (TPE) e.g., polyether block amide, thermoplastic polyurethane, polyethylene, nylon, or the like. The outer layer 130 may extend from the proximal end 104 to the distal end 106 of the elongate body 110. The tube member 140 can be incorporated between the inner liner 120 and the outer layer 130 and extends partially or substantially the entire length of the elongate body 110. The tube member 140 can be constructed from metal such as stainless steel, nitinol, or from polymers such as polyether-ether-ketone (PEEK), or any combinations thereof. The tube member 140 provides reinforcement for the intravascular device 100 to prevent kinking or flattening of the inner lumen 112 of the elongate body 110 in navigation through a tortuous vasculature. According to embodiments of the disclosure, the tube member 140 comprises a plurality of cuts 142 with a pattern and geometry that provide the intravascular device 100 with a desired balance of bending flexibility, torsional rigidity, and tensile strength, to be described in greater detail below.

Figure 2:
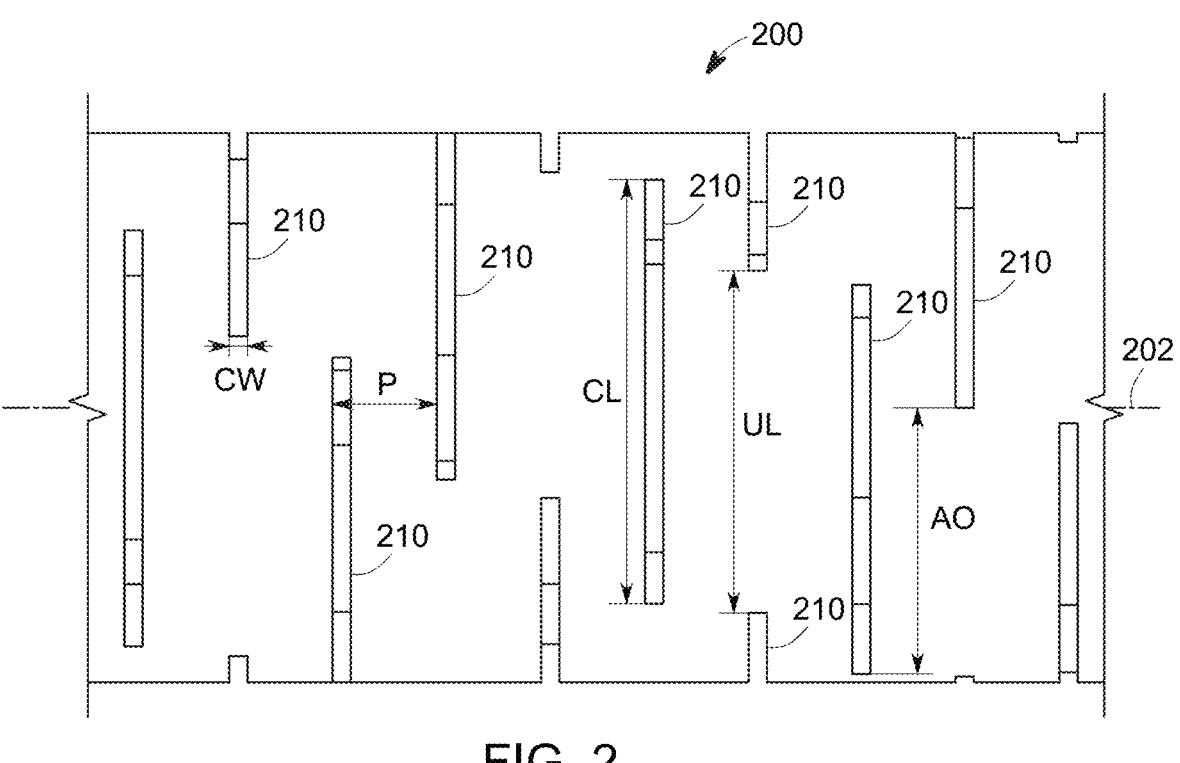
FIG. 2 is a simplified illustration of a segment or portion of an example tube member showing a plurality of vertical cuts according to embodiments of the disclosure.

FIG. 2 depicts a portion of an example tube member 200 according to embodiments of the disclosure, which can be used as the tube member 140 of the intravascular device 100 shown in FIG. 1. The portion of the tube member 200 comprises a plurality of cuts 210 extending circumferentially around a longitudinal axis 202 of the tube member 200. The plurality of cuts 210 shown in FIG. 2 are vertical and/or segmented at a plurality of axial locations of the tube member 200. As used herein, the term "axial location" refers to a location along the longitudinal axis 202 of the tube member 200. The term "vertical cut" may be used herein to refer to a cut or slot that extends circumferentially along a path normal to the longitudinal axis 202 of the tube member 200.

With reference to FIG. 2, in describing various embodiments of the disclosure the term "cut length" (CL) may be used to indicate the distance in the circumferential direction that a vertical cut travels. The cut length can be expressed in degrees to normalize for different tube outer diameters. For example, a cut length can be expressed as X degrees out of a 360-degree circumference. The term "uncut length" (UL) may be used to indicate the distance in the circumferential direction between sequential or adjacent cuts, i.e., from the end of one cut to the start of the next cut. Similarly, an uncut length can be expressed in degrees to normalize for different tube outer diameters, e.g., X degrees out of a 360-degree circumference. According to embodiments of the disclosure, a portion of the tube member 200 includes vertical cuts with a longer cut length to increase the flexibility of the tube member. In some embodiments, a portion of the tube member 200 includes vertical cuts with a longer uncut length between sequential or adjacent cuts to increase the stiffness and/or improve the torque response of the tube member. According to some embodiments of the disclosure, a combined cut length and uncut length in a 360—circumference can add up to a factor of 360 degrees, i.e., 60 degrees, 120 degrees, 180 degrees, etc. By way of example, if two vertical cuts are provided at a given axial location of the tube member, then the cut length of a vertical cut and an uncut length between two vertical cuts can add up to 180 degrees. If three vertical cuts are provided at a given axial location of the tube member, then the cut length of a cut and an uncut length between two vertical cuts can add up to 120 degrees.

With reference to FIG. 2, in describing various embodiments of the disclosure the term "pitch" (P) may be used to indicate the distance in the axial direction between two adjacent vertical cuts 210 of the tube member 200. The pitch can be defined as the distance between the proximal side of one cut and the proximal side of the next adjacent cut in the axial direction. The pitch can also be defined as the distance between the distal side of one cut and the distal side of the next adjacent cut in the axial direction. In some embodiments, a portion of the tube member 200 includes a plurality of vertical cuts with a relatively small pitch to make the tube member more flexible. In some embodiments, a portion of the tube member 200 includes a plurality of vertical cuts with a relatively large pitch to make the tube member stiffer and/or to increase torque response.

With reference still to FIG. 2, in describing various embodiments of the disclosure the term "cut width" (CW) may be used to refer to the width of a given cut pattern at the outer surface of the tube member 200. According to embodiments of the disclosure, a portion of the tube member 200 may include a plurality of vertical cuts with a greater cut width to make the portion more flexible, or include a plurality of cuts with a smaller cut width to increase torque response. In describing various embodiments of the disclosure, the term "angle offset" (AO) may be used to indicate a cut pattern where a group of cuts at a given axial location is offset from a successive group of cuts at the next axial location by a set angle, to avoid stiffening the tube by locating uncut segments adjacent to each other.

Figure 3:
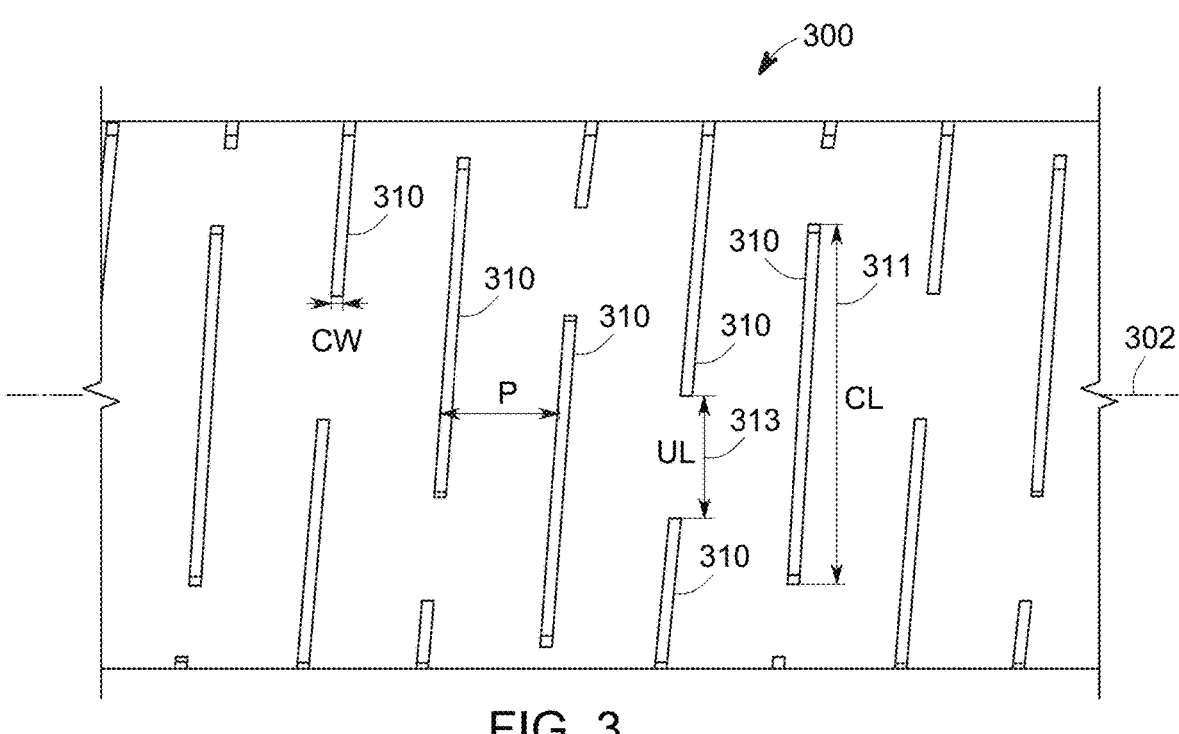
FIG. 3 is a simplified illustration of a segment or portion of an example tube member showing a plurality of helical cuts according to embodiments of the disclosure.
Figure 4:
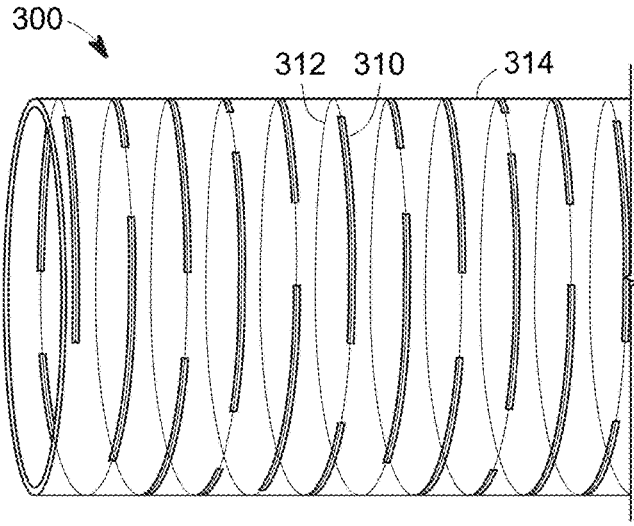
FIG. 4 is a simplified illustration of a segment or portion of an example tube member showing a helix around the outer surface of the tube member and a plurality of cuts that follows or travels along the helix.

FIG. 3 depicts a portion of an example tube member 300 according to alternative embodiments of the disclosure, which can be used as the tube member 140 of the intravascular device 100 shown in FIG. 1. The portion of the tube member 300 comprises a plurality of cuts 310 circumferentially extending around a longitudinal axis 302 of the tube member 300. The plurality of cuts 310 shown in FIG. 3 are spiral or helical around the longitudinal axis 302 of the tube member 300. As used herein, the term "helical cut" refers to a cut or slot that extends circumferentially along a path helical around the longitudinal axis of the tube member. FIG. 4 schematically shows a helical path 312 on the outer surface 314 of a tube member 300, and a plurality of cuts 310 that follow or travel along the helical path 312. It should be noted that the helix 312 can travel in a clockwise or counterclockwise direction around the tube. The patterns disclosed herein are independent of the direction of helix rotation.

Returning to FIG. 3, in describing various embodiments of the disclosure the term "cut length" (CL) may be used to indicate the distance in the circumferential direction that a helical cut travels, measured in the vertical direction. In FIG. 3, reference 310 indicates a helical cut. Reference 311 indicates the distance in the vertical direction of the helical cut 310, and is referred to as the "cut length" of the helical cut 310. The cut length can be expressed in degrees to normalize for different tube outer diameters. For example, the cut length 311 of a helical cut 310 can be expressed as X degrees out of a 360-degree circumference. The term "uncut length" (UL) is used to indicate the distance in the circumferential direction between sequential or adjacent helical cuts measured in the vertical direction i.e., from the end of one cut to the start of the next cut. In FIG. 3, reference 313 indicates the distance between sequential helical cuts 310 measured in the vertical direction, and is referred as "uncut length." An uncut length can be expressed in degrees to normalize for different tube outer diameters, e.g., X degrees out of a 360-degree circumference. According to embodiments of the disclosure, a portion of the tube member 300 includes helical cuts with a relatively long cut length to increase the flexibility of the tube member. In some embodiments, a portion of the tube member 300 includes helical cuts with a relatively long uncut length to increase the stiffness and/or improve the torque response of the tube member. Due to the helical nature of the cut pattern, it is unnecessary that the cut length of a helical cut and the uncut length between the sequential helical cuts add up to 360 degrees or to a factor of 360 degrees such as 60 degrees, 120 degrees, 180 degrees, etc. In an embodiment of the disclosure, the cut length of a helical cut and the uncut length between the sequential helical cuts do not add up to 360 degrees or to a factor of 360 degrees, to avoid the effect of stiffening the tube member by locating uncut segments adjacent to each other. In the vertical/segmented cut pattern shown in FIG. 2, the cut or group of cuts may have an angle offset to mitigate the tube stiffening effect.

With reference to FIG. 3, in describing various embodiments of the disclosure the term "pitch" (P) is used to indicate the distance in the axial direction between adjacent helical cuts 310 of the tube member 300. The pitch can be the distance between the proximal side of one cut and the proximal side of the next cut in the axial direction. The pitch can also be the distance between the distal side of one cut and the distal side of the next cut in the axial direction. In some embodiments, a portion of the tube member includes a plurality of helical cuts with a relatively small pitch to make the tube member more flexible. In some embodiments, a portion of the tube member includes a plurality of helical cuts with a relatively large pitch to make the tube member stiffer and increase torque response.

Figure 5A:
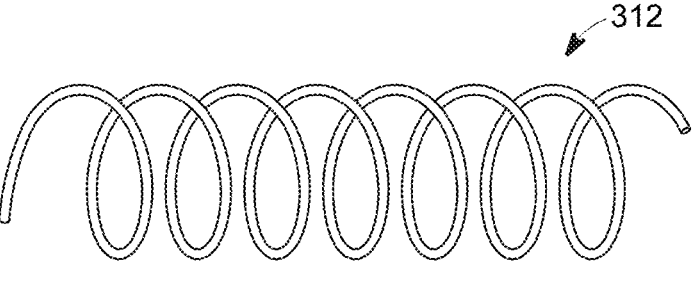
FIGS. 5A-5C are simplified illustrations showing example helical paths along which cuts can be created on the outer surface of a tube member according to embodiments of the disclosure.

In accordance with some embodiments of the disclosure, at least a portion of the tube member 300 may include a plurality of helical cuts 310 with a constant pitch, i.e., the helical path or helix 312 that the plurality of cuts follows has a constant pitch. FIG. 5A schematically shows an example helix 312 with a constant pitch.

Figure 5B:
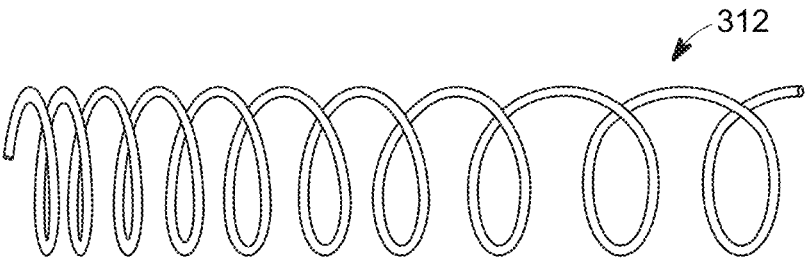
Figure 5C:
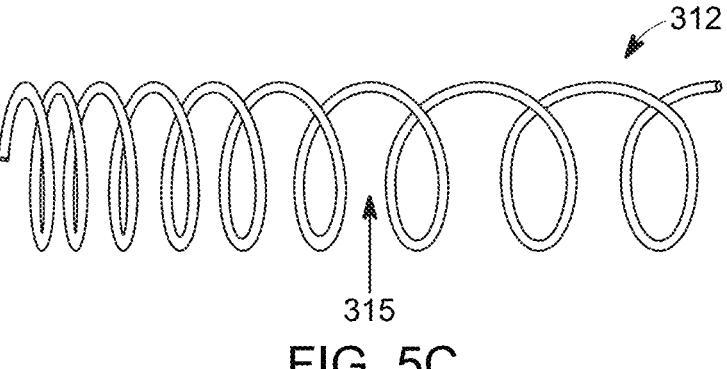

In accordance with some embodiments of the disclosure, at least a portion of the tube member 300 may include a plurality of helical cuts 310 with a varying pitch along the length or longitudinal axis of the tube member, as shown in FIGS. 5B-5C. A varying pitch of helical cuts can result in a varying stiffness or flexibility of the tube member along the length of the tube member. The pitch can vary linearly along the longitudinal axis of the tube member, where the pitch increases or decrease with a constant variant, as shown in FIG. 5B. In some embodiments, the varying pitch of the helical cuts 310 may include an instantaneous step or switch 315, as shown in FIG. 5C. The pitch step or switch 315 may indicate a change from a smaller constant pitch to a greater constant pitch, or a change from a constant pitch to a linearly increasing/decreasing pitch, or a change from one linearly increasing/decreasing pitch to another linearly increasing/decreasing pitch, and so on. In the same way that pitch can be varied in these many ways, so can the cut lengths, uncut lengths, and cut widths be varied linearly or be changed instantaneously.

Figure 6:
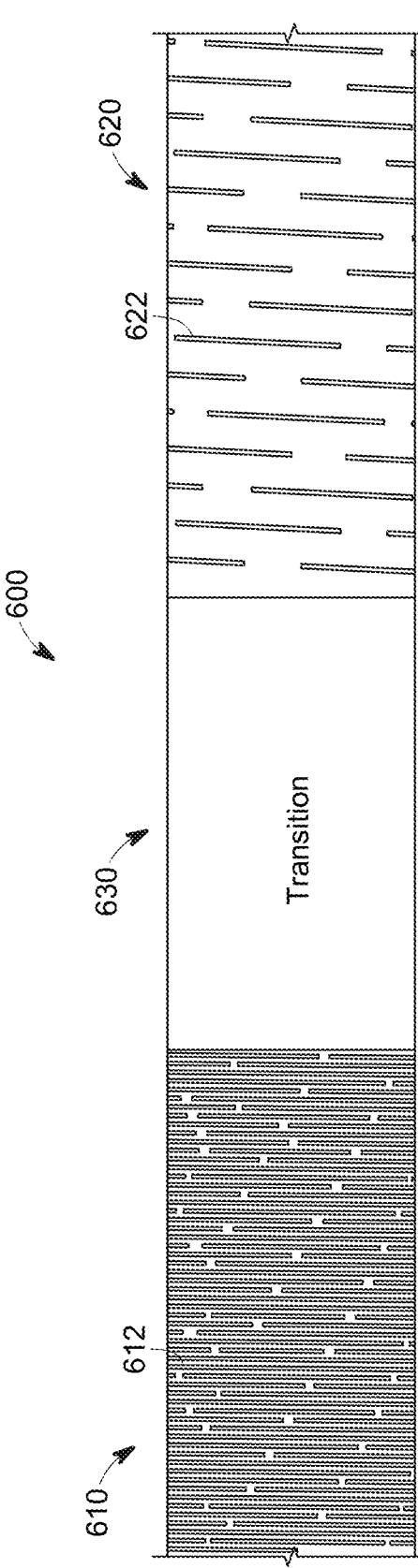
FIG. 6 is a simplified illustration of an example tube member comprising multiple segments or portions with different cut patterns and/or parameters according to embodiments of the disclosure.

With reference to FIG. 6, according to embodiments of the disclosure an example tube member 600 comprises a distal portion 610, a proximal portion 620, and optionally a transition portion 630 between the distal portion 610 and the proximal portion 620. Each of the distal portion 610, the proximal portion 620, and the transition portion 630 comprise a plurality of cuts extending circumferentially around the longitudinal axis of the tube member 600. The pattern and/or parameters of the plurality of cuts of the distal portion 610, the proximal portion 620, and the transition portion 630 are configured to impart the tube member 600 a desired profile e.g., a more flexible distal portion 610, a stiffer proximal portion 620, and a gradual or smooth transition portion 630. The pattern and/or parameters of the plurality of cuts provide a desired balance between the flexibility, the torque response, and the tensile strength, allowing an intravascular device comprising the tube member 600 to navigate a tortuous anatomy while also giving it support to be pushed further into the body.

With reference to FIG. 6, the distal portion 610 can include a plurality of cuts 612 with a first cut length (CL1), a first uncut length (UL1), a first cut width (CW1), and a first pitch (P1). Each of CL1, UL1, CW1, and P1 can be a constant value or vary linearly over the distal portion 610 or comprise an instantaneous change. The proximal portion 620 can include a plurality of cuts 622 with a second cut length (CL2), a second uncut length (UL2), a second cut width (CW2), and a second pitch (P2). Each of CL2, UL2, CW2, and P2 can be a constant value or vary linearly over the proximal portion 620 or comprise an instantaneous change. The transition portion 630 can include a plurality of cuts (not shown in FIG. 6) with a third cut length (CL3), a third uncut length (UL3), a third cut width (CW3), and a third pitch (P3). Each of CL3, UL3, CW3, and P3 can be a constant value or vary linearly over the transition portion 630 or comprise an instantaneous change.

According to embodiments of the disclosure, the first pitch of the cuts 612 of the distal portion 610 is less than the second pitch of the cuts 622 of the proximal portion 620. In an embodiment, the first cut length of the cuts 612 of the distal portion 610 is greater than the second cut length of the cuts 622 of the proximal portion 620. In an embodiment, the first uncut length of the cuts 612 of the distal portion 610 is less than the second uncut length of the cuts 622 of the proximal portion 620. In an embodiment, the first pitch of the cuts 612 of the distal portion 610 is less than the second pitch of the cuts 622 of the proximal portion 620, the first cut length of the cuts 612 of the distal portion 610 is greater than the second length of the cuts 622 of the proximal portion 620, and the first uncut length of the cuts 612 of the distal portion 610 is less than the second uncut length of the cuts 622 of the proximal portion 620.

According to embodiments of the disclosure, a combined first cut length and first uncut length is greater than or equal to a combined second cut length and second uncut length.

According to embodiments of the disclosure, the plurality of cuts 612 of the distal portion 610 has a first cut width (CW1), the plurality of cuts 622 of the proximal portion 620 has a second cut width (CW2), and the first cut width is greater than the second cut width. Alternatively, the first cut width of cuts 612 of the distal portion 610 is substantially the same as the second cut width of cuts 622 of the proximal portion 620.

According to embodiments of the disclosure, the plurality of cuts 612 of the distal portion 610 comprises vertical cuts, and the plurality of cuts 622 of the proximal portion 620 comprises helical cuts. Alternatively, the plurality of cuts 612 of the distal portion 610 and the plurality of cuts 622 of the proximal portion 620 are both helical cuts. In some embodiments, the plurality of cuts 612 of the distal portion 610 and the plurality of cuts 622 of the proximal portion 620 are both vertical cuts. In general, a vertical cut pattern allows for a smaller pitch and a greater cut length.

By way of example, a tube member 600 according to embodiments of the disclosure comprises a distal portion 610 extending a length of 10 cm or less from the distal end extremity of the tube member, and a proximal portion 620 extending from an axial location at 15 cm or more from the distal end extremity. Each of the distal portion 610 and the proximal portion 620 of the tube member 600 includes a plurality of helical cuts. In the distal portion 610 of the tube member 600, the plurality of the helical cuts 612 has a pitch in the range between 0.03 mm and 0.30 mm, a cut width in the range between 0.0008 inches to 0.0060 inches (0.020 mm to 0.160 mm), an uncut length in the range from 3 degrees to 15 degrees, a cut length in the range from 60 degrees to 177 degrees, and a combined cut length and uncut length in the range between 75 and 180 degrees. In the proximal portion 620 of the tube member 600, the plurality of the helical cuts 622 has a pitch in the range between 0.10 mm and 1.00 mm, a cut width in the range between 0.0008 inches to 0.0020 inches (0.020 mm to 0.051 mm), an uncut length in the range from 15 degrees to 40 degrees, a cut length in the range from 60 degrees to 165 degrees, and a combined cut length and uncut length in the range between 75 and 180 degrees.

It should be noted that the above specific dimensions, sizes, and degrees are provided for a thorough understanding of the disclosure. The scope of the claims and the disclosure is not limited to the specific dimensions, sizes, and degrees.

In conjunction with each of the above embodiments, the optional transition portion 630 of the tube member 600 comprises a plurality of cuts having a cut pattern and/or parameters configured to facilitate a smooth or gradual transition from a more flexible distal portion 610 to a stiffer proximal portion 620.

Figure 7:
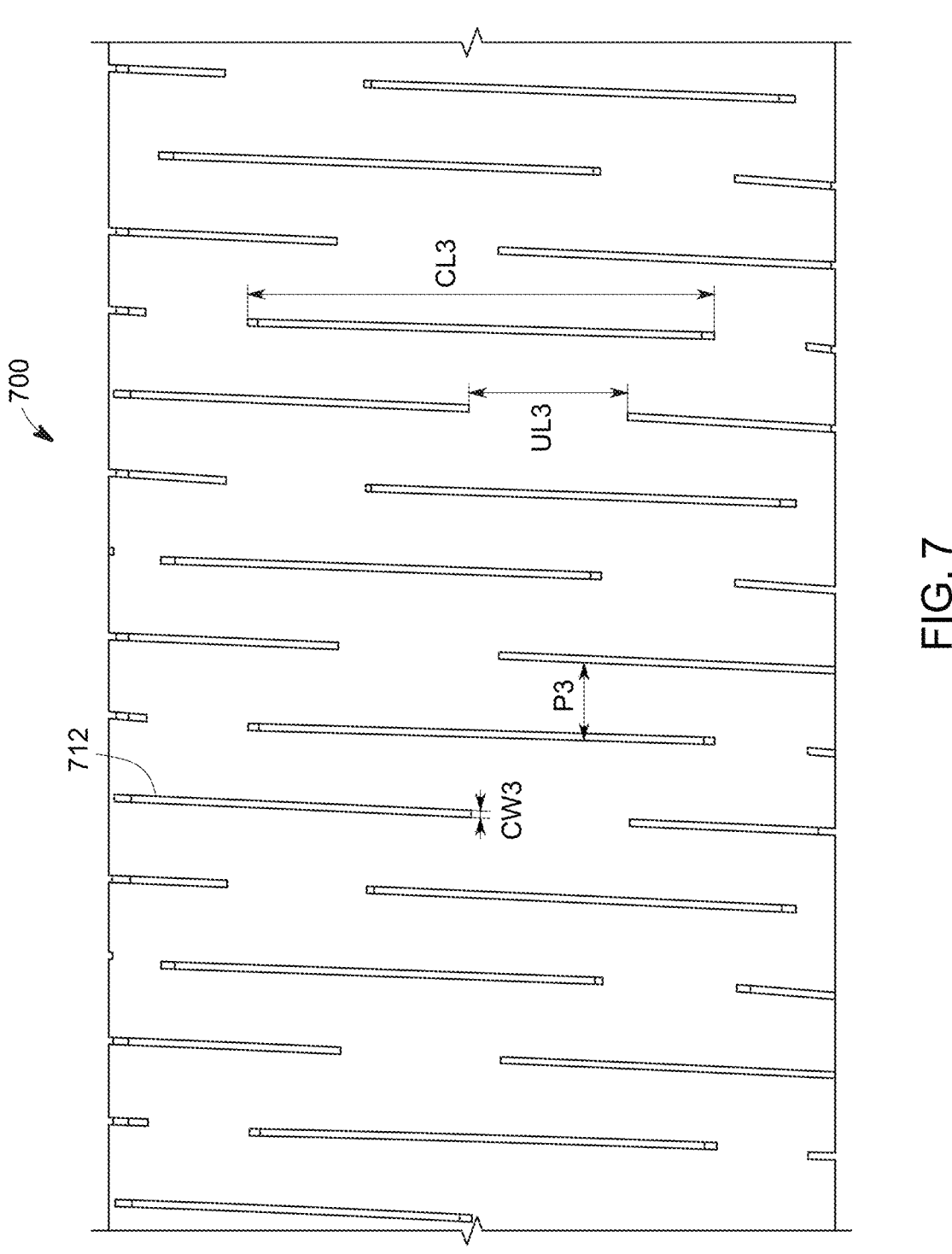
FIG. 7 is a simplified illustration of a segment or portion of an example tube member showing a plurality of helical cuts with a constant pitch, a constant cut length, and a constant uncut length according to embodiments of the disclosure.

FIG. 7 depicts an example tube segment 700 according to embodiments of the disclosure, which can be used as the transition portion 630 of the tube member 600. As shown, the tube segment 700 comprises a plurality of helical cuts 712. The plurality of helical cuts 712 has a constant pitch (P3), a constant cut length (CL3), and a constant uncut length (UL3). In an embodiment, the pitch (P3) of the helical cuts 712 of the tube segment 700 is greater than or equal to the pitch (P1) of the cuts 612 of the distal portion 610 of the tube member 600. Alternatively, or in addition, the pitch (P3) of the helical cuts 712 of the tube segment 700 is less than or equal to the pitch (P2) of the cuts 622 of the proximal portion 620 of the tube member 600. The cut length (CL3)

of the helical cuts 712 of the tube segment 700 can be less than or equal to the cut length (CL1) of the cuts 612 of the distal portion 610 of the tube member 600. Alternatively, or in addition, the cut length (CL3) of the helical cuts 712 of the tube segment 700 can be greater than or equal to the cut length (CL2) of the cuts 622 of the proximal portion 620 of the tube member 600. The uncut length (UL3) of the helical cuts 712 of the tube segment 700 can be greater than or equal to the uncut length (UL1) of the cuts 612 of the distal portion 610 of the tube member 600, and/or less than or equal to the uncut length (UL3) of the cuts 622 of the proximal portion 620 of the tube member 600. A combined cut length (CL3) and uncut length (UL3) of the cuts 712 of the tube segment 700 can be less than or equal to 180 degrees.

Figure 8:
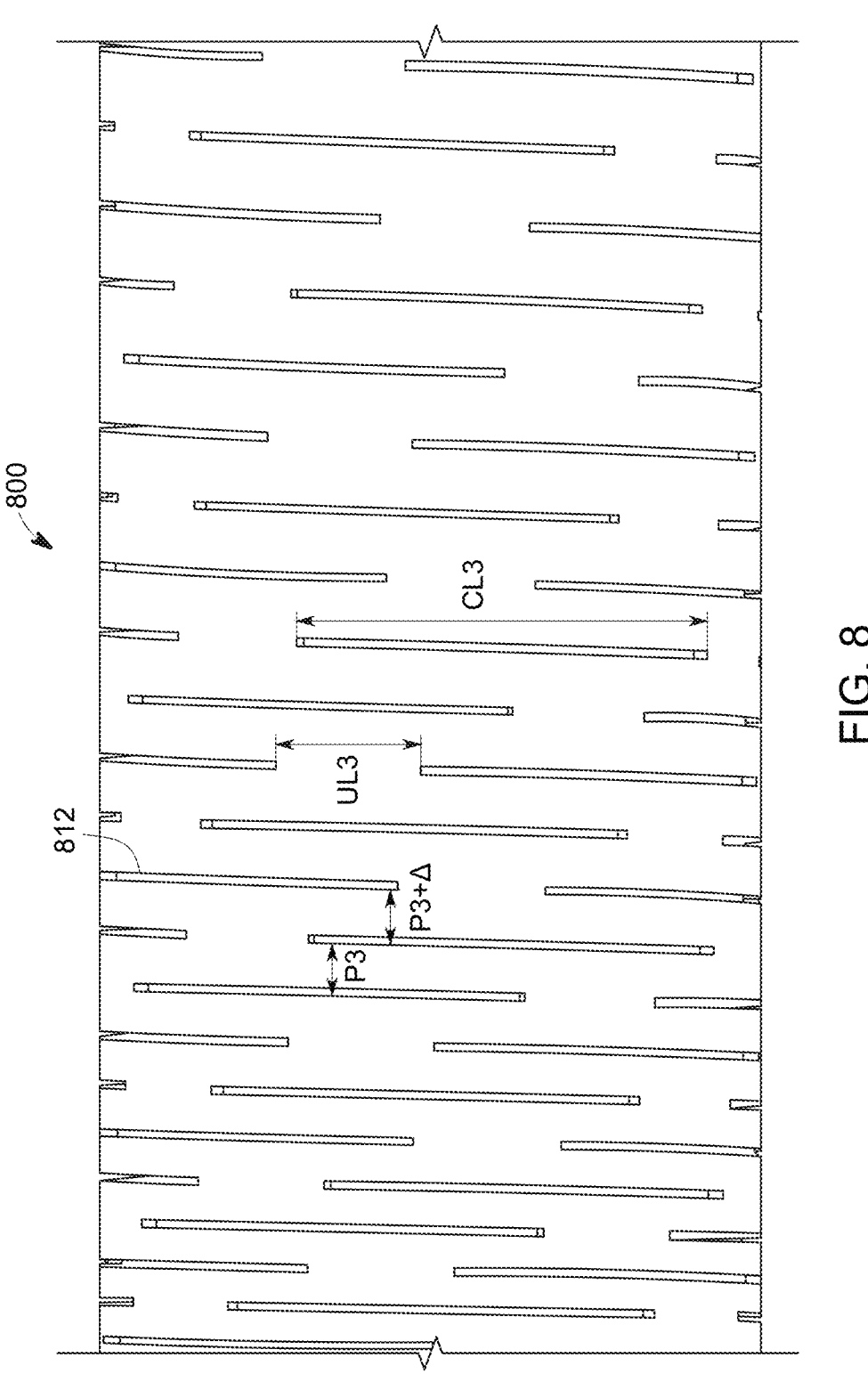
FIG. 8 is a simplified illustration of a segment or portion of an example tube member showing a plurality of helical cuts with an increasing pitch, a constant cut length, and a constant uncut length according to embodiments of the disclosure.

FIG. 8 depicts another example tube segment 800 according to embodiments of the disclosure, which can be used as the transition portion 630 of the tube member 600. As shown, the tube segment 800 comprises a plurality of helical cuts 812. The plurality of helical cuts 812 has a proximally increasing pitch (P3, P3+Δ), a constant cut length (CL3), and a constant uncut length (UL3). The pitch (P3, P3+Δ) of the helical cuts 812 the tube segment 800 can be greater than the pitch (P1) of the cuts 612 of the distal portion 610 of the tube member 600, and increases in the proximal direction. The pitch (P3, P3+Δ) of the helical cuts 812 the tube segment 800 can linearly increase along the longitudinal axis of the tube segment 800, or non-linearly increase along the longitudinal axis of the tube segment 800 e.g., including an instantaneous pitch switch. While proximally increasing, the pitch (P3 or P3+Δ) of the helical cuts 812 the tube segment 800 can be less than the pitch (P2) of the cuts 622 of the proximal portion 620 of the tube member 600. The cut length (CL3) of the helical cuts 812 the tube segment 800 can be less than or equal to the cut length (CL1) of the cuts 612 of the distal portion 610 of the tube member 600, and/or, greater than or equal to the cut length (CL2) of the cuts 622 of the proximal portion 620 of the tube member 600. The uncut length (UL3) of the helical cuts 812 the tube segment 800 can be greater than or equal to the uncut length (UL1) of the cuts 612 of the distal portion 610 of the tube member 600, and/or, less than or equal to the uncut length (UL2) of the cuts 622 of the proximal portion 620 of the tube member 600. A combined cut length (CL3) and uncut length (UL3) of the cuts 812 of the tube segment 800 can be less than or equal to 180 degrees.

Figure 9:
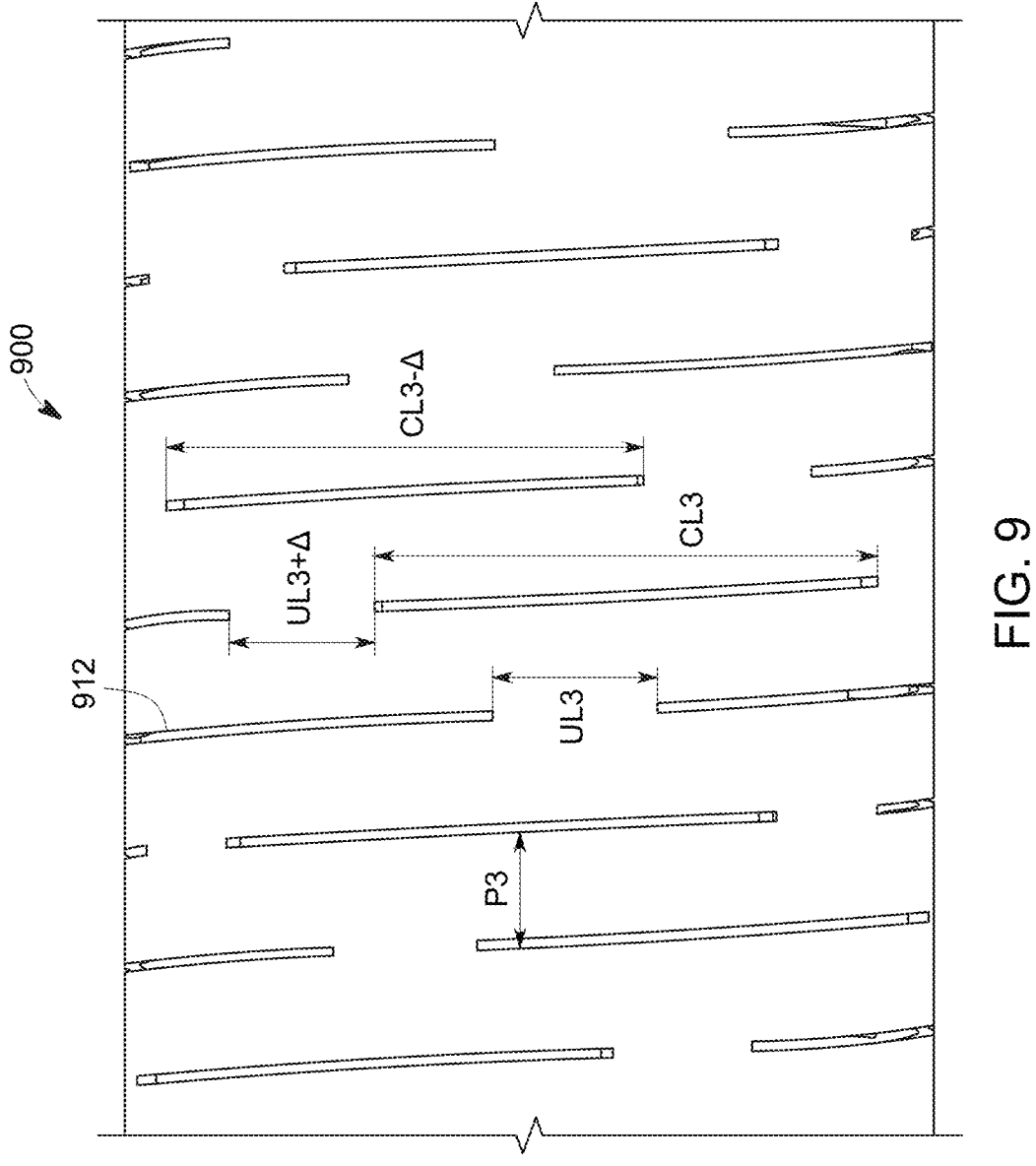
FIG. 9 is a simplified illustration of a segment or portion of an example tube member showing a plurality of helical cuts with a constant pitch, a decreasing cut length, and an increasing uncut length according to embodiments of the disclosure.

FIG. 9 depicts another example tube segment 900 according to embodiments of the disclosure, which can be used as the transition portion 630 of the tube member 600. As shown, the tube segment 900 comprises a plurality of helical cuts 912. The plurality of helical cuts 912 has a constant pitch (P3), a proximally decreasing cut length (CL3, CL3–Δ), and a proximally increasing uncut length (UL3, UL3+Δ). The constant pitch (P3) of the helical cuts 912 of the tube segment 900 can be greater than or equal to the pitch (P1) of the cuts 612 of the distal portion 610 of the tube member 600, and/or, less than or equal to the pitch (P2) of the cuts 622 of the proximal portion 620 of the tube member 600. The cut length (CL3, CL3–Δ) of the helical cuts 912 of the tube segment 900 can be less than the cut length (CL1) of the cuts 612 of the distal portion 610 of the tube member 600, and decreases linearly or non-linearly in the proximal direction e.g., including an instantaneous switch. While proximally decreasing, the cut length (CL3, CL3–Δ) of the helical cuts 912 of the tube segment 900 can be greater than the cut length (CL2) of the cuts 622 of the proximal portion 620 of the tube member 600. The uncut length (UL3, UL3+Δ) of the helical cuts 912 of the tube segment 900 can be greater than the uncut length (UL1) of the cuts 612 of the distal portion 610 of the tube member 600, and increases linearly or non-linearly in the proximal direction e.g., including an instantaneous change. While proximally increasing, the uncut length (UL3, UL3+Δ) of the helical cuts 912 of the tube segment 900 can be less than the uncut length of (UL2) of the cuts 622 of the proximal portion 620 of the tube member 600. A combined cut length (CL3) and uncut length (UL3) of the helical cuts 912 of the tube segment 900 can be less than or equal to 180 degrees.

Figure 10:
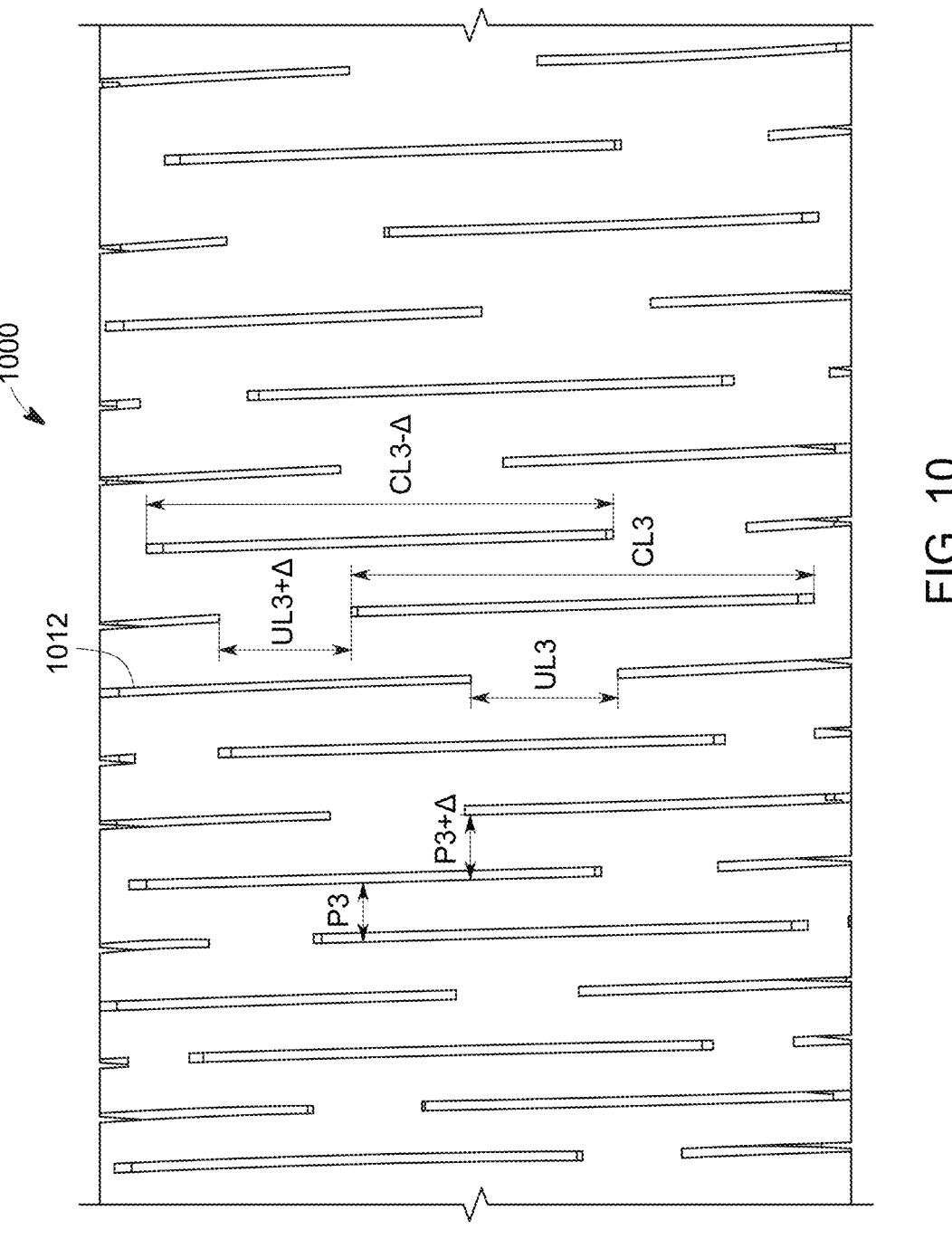
FIG. 10 is a simplified illustration of a segment or portion of an example tube member showing a plurality of helical cuts with an increasing pitch, a decreasing cut length, and an increasing uncut length according to embodiments of the disclosure.

FIG. 10 depicts a further tube segment 1000 according to embodiments of the disclosure, which can be used as the transition portion 630 of the tube member 600. As shown, the tube segment 1000 comprises a plurality of helical cuts 1012. The plurality of helical cuts 1012 has a proximally increasing pitch (P3, P3+Δ), a proximally decreasing cut length (CL3, CL3–Δ), and a proximally increasing uncut length (UL3, UL3+Δ). The pitch (P3, P3+Δ) of the helical cuts 1012 of the tube segment 1000 can be greater than the pitch (P1) of the cuts 612 of the distal portion 610 of the tube member 600, and increases in the proximal direction. The proximally increasing pitch (P3, P3+Δ) can linearly or non-linearly increase along the longitudinal axis of the tube segment 1000. While proximally increasing, the pitch (P3, P3+Δ) of the helical cuts 1012 the tube segment 1000 can be less than the pitch (P2) of the cuts 622 of the proximal portion 620 of the tube member 600. The cut length (CL3, CL3–Δ) of the helical cuts 1012 of the tube segment 1000 can be less than the cut length (CL1) of the cuts 612 of the distal portion 610 of the tube member 600, and decreases linearly or non-linearly in the proximal direction. While proximally decreasing, the cut length (CL3, CL3–Δ) of the helical cuts 1012 of the tube segment 1000 can be greater than the cut length (CL2) of the cuts 622 of the proximal portion 620 of the tube member 600. The uncut length (UL3, UL3+Δ) of the helical cuts 1012 the tube segment 1000 can be greater than the uncut length (UL1) of the cuts 612 of the distal portion 610 of the tube member 600, and increases linearly or non-linearly in the proximal direction. While proximally increasing, the uncut length (UL3, UL3+Δ) of the helical cuts 1012 the tube segment 1000 can be less than the uncut length (UL2) of the cuts 622 of the proximal portion 620 of the tube member 600. A combined cut length (CL3) and uncut length (UL3) of the helical cuts 1012 of the tube segment 1000 can be less than or equal to 180 degrees.

Figure 11:
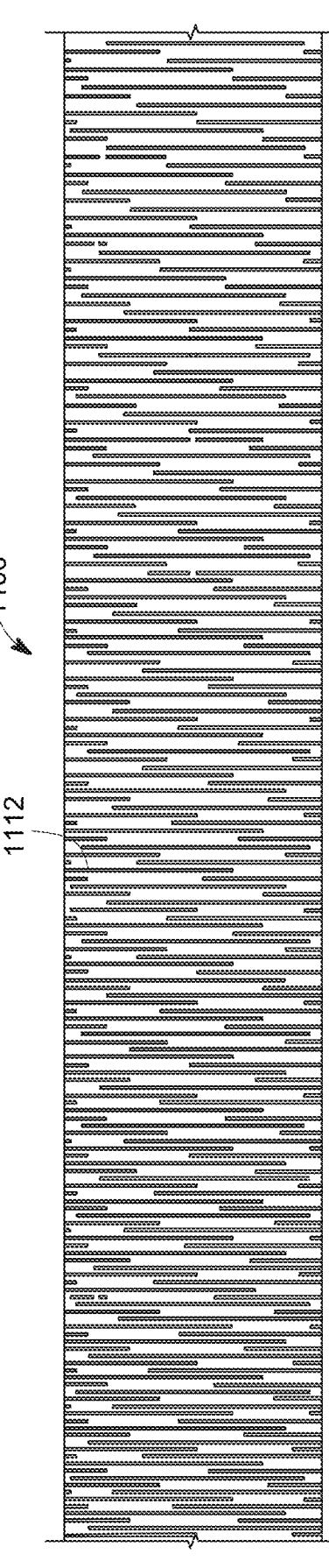
FIG. 11 is a simplified illustration of a segment or portion of an example tube member showing a plurality of vertical cuts with an increasing pitch, a decreasing cut length, and an increasing uncut length according to embodiments of the disclosure.

FIG. 11 depicts a further tube segment 1100 according to embodiments of the disclosure, which can be used as the transition portion 630 of the tube member 600. As shown, the tube segment 1100 comprises a plurality of vertical cuts 1112 segmented at a plurality of axial locations of the tube segment 1100. The plurality of vertical cuts 1112 of the tube segment 1100 define a proximally increasing pitch (P3, P3+Δ), a proximally decreasing cut length (CL3, CL3–Δ), and a proximally increasing uncut length (UL3, UL3+Δ). The pitch (P3, P3+Δ) of the helical cuts 1112 of the tube segment 1100 can be greater than the pitch (P1) of the cuts 612 of the distal portion 610 of the tube member 600, and increases linearly or non-linearly in the proximal direction. While proximally increasing, the pitch (P3, P3+Δ) of the helical cuts 1112 the tube segment 1100 can be less than the pitch (P2) of the cuts 622 of the proximal portion 620 of the tube member 600. The cut length (CL3, CL3–Δ) of the helical cuts 1112 of the tube segment 1100 can be less than the cut length (CL1) of the cuts 612 of the distal portion 610 of the tube member 600, and decreases linearly or non-linearly in the proximal direction. While proximally decreasing, the cut length (CL3, CL3–Δ) of the helical cuts 1112 of the tube segment 1100 can be greater than the cut length (CL2) of the cuts 622 of the proximal portion 620 of the tube member 600. The uncut length (UL3, UL3+Δ) of the helical cuts 1112 of the tube segment 1100 can be greater than the uncut length (UL1) of the cuts 612 of the distal portion 610 of the tube member 600, and increases linearly or non-linearly in the proximal direction. While proximally increasing, the uncut length (UL3, UL3+Δ) of the helical cuts 1112 the tube segment 1000 can be less than the uncut length (UL2) of the cuts 622 of the proximal portion 620 of the tube member 600. A combined cut length (CL3, CL3−Δ) and uncut length (UL3, UL3+Δ) of the helical cuts 1112 of the tube segment 1000 can be a factor of 360 degrees, i.e., 60 degrees, 120 degrees, 180 degrees, etc.

It should be noted that while embodiments of the tube segments 700, 800, 900, and 1000 depicted in FIGS. 7-9 are described in connection with a transition portion of a tube member such as transition portion 630 of tube member 600 shown in FIG. 6, the cut patterns and parameters described above and shown in FIGS. 7-9 can be used in a distal portion, a proximal portion, or the entire length of a tube member to be included in an intravascular device or other medical devices.

Embodiments of the disclosure provides a method of making intravascular devices. The method utilizes laser to cut a tube member in a pattern and/or geometry unattainable by the conventional techniques. The novel cutting pattern and/or geometry provides the intravascular device with a desired balance between bending flexibility, torsional rigidity, and tensile strength. Beneficially, the laser cutting techniques described herein allow for more precise control over the design inputs, e.g., providing a wide range of cut width by e.g., adjusting the width of the laser beam. With traditional micro-machining, the cut width must be equal to the width of a cutting element such as a physical saw.

Figure 12:
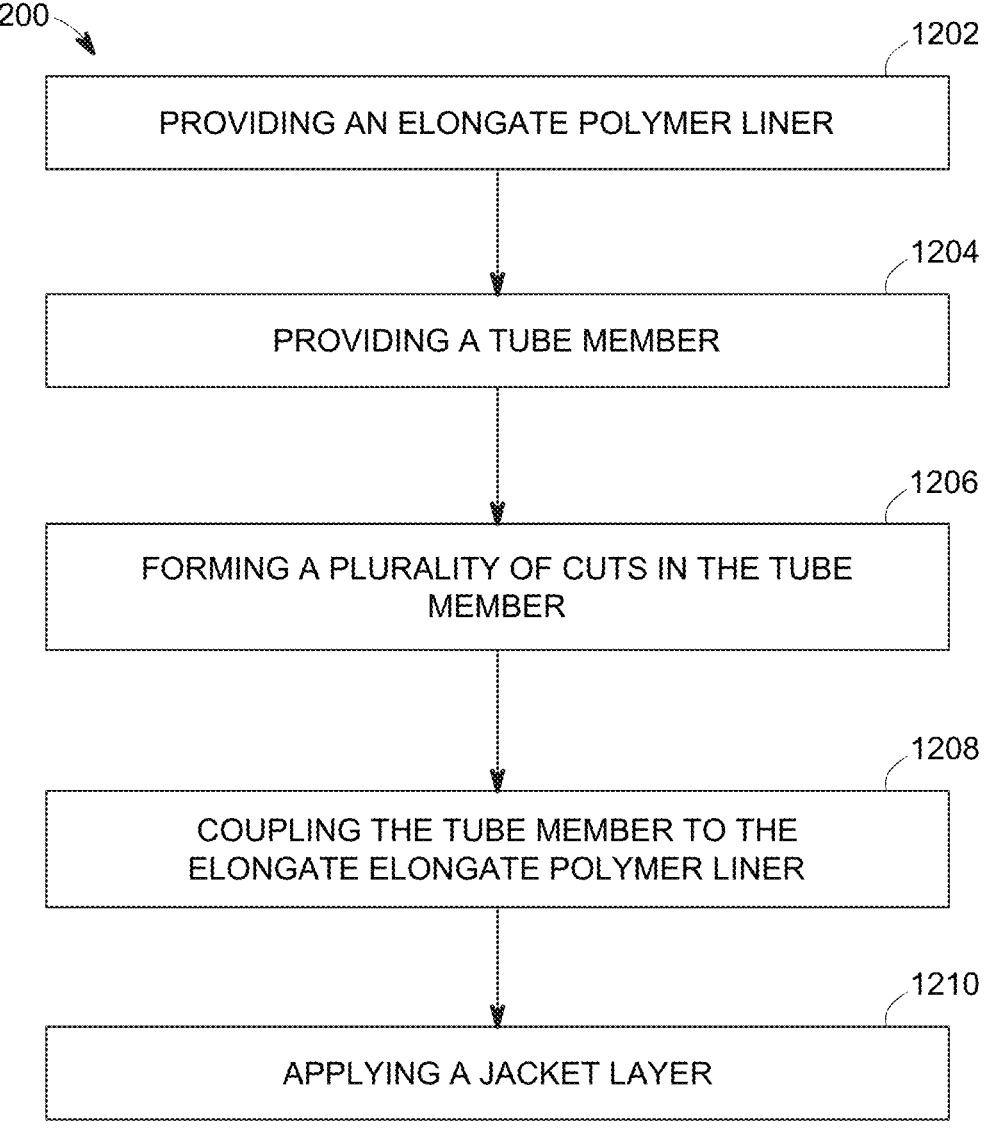
FIG. 12 is a flowchart illustrating example steps of a method of making intravascular devices according to embodiments of the disclosure.

FIG. 12 is a flowchart illustrating example steps of a method 1200 of making intravascular devices according to embodiments of the disclosure. The method is described in conjunction with an embodiment of making a catheter device. It should be noted that steps of the method 1200 can be implemented to make other intravascular devices such as guidewires. At step 1202, an elongate polymer liner is provided. The polymer liner can be constructed from a biocompatible lubricious or low-friction material to provide a smooth surface for advancement of devices or objects through the inner lumen. Suitable lubricious materials include but are not limited to polytetrafluoroethylene (PTFE), fluorinated ethylene propylene (FEP), polyether block amide (PEBA), and other suitable polymeric materials. The polymeric materials may include additives such as siloxane. The polymer liner may be a single continuous tubular member extending substantially the entire axial length of the catheter device. The polymer liner may also be a multi-piece or multi-region construction wherein each piece or region is made of different materials having different properties such as flexibility or rigidity. For example, the proximal section or region of the polymer liner may be made of relatively stiff materials for better pushability and torque-ability whereas the distal section of the polymer liner can be made of relatively more elastic material for better steerability and trackability. The polymer liner can be constructed by extrusion or any other suitable methods.

The polymer liner may have a length sufficient for reaching to a target site within the patient. Generally, the length of the polymer liner ranges between 5 cm and 300 cm. The distal section of the polymer liner may be tapered towards the distal end to provide more bending flexibility. The proximal section of the polymer liner may have an increased diameter to maintain pushability and torsional rigidity of the catheter device. Depending on applications, the polymer liner may have an inner diameter ranging from 0.012 inches to 0.115 inches and a wall thickness from 0.00025 inches to 0.0030 inches. In an embodiment, catheter devices having an outer diameter equal to or less than 0.125 inches can be made according to the method 1200 of the disclosure.

At step 1204, a tube member is provided. The tube member may be made of a metal, metal alloy, polymer, metal-polymer composite, or any combination thereof. Suitable metals and metal alloys for the tube member include stainless steel, nickel-titanium alloy or Nitinol, or other nickel alloys such as cobalt-chromium alloys, nickel-molybdenum alloys, nickel-copper alloys, nickel-cobalt alloys, other nickel-iron alloys, nickel-tungsten alloys, cobalt-chromium-molybdenum alloys, and so on. Suitable polymers for the tube member include polytetrafluoroethylene (PTFE), fluorinated ethylene propylene (FEP), polyether-ether-ketone (PEEK), and other suitable polymeric materials.

The tube member may have a length covering at least a portion of the length of the polymer liner. In some embodiments, the tube member may have a length that covers the entire length of the polymer liner. By way of example, the tube member may have a length ranging e.g., from 5 cm to 300 cm for application in a catheter device. It should be noted that embodiments of the disclosure can find applications in making other medical devices such as a guidewire device, which can have a length suitable for application as a guidewire device.

The tube member may have an outer diameter, an inner diameter, and a wall thickness selected to provide one or more desired base properties, such as rigidity, flexibility, tensile strength, torque response etc. for a particular application. In general, if the outer diameter of the tube member is increased while the wall thickness is decreased, the tube member can have the same bending stiffness with an increased torque response, at the cost of some mechanical strength. In another example, if the outer diameter of the tube is decreased while the wall thickness is increased, the tube member can have increased axial rigidity with the same bending stiffness, at the cost of reduced torque response.

At step 1206, a plurality of cuts or slots are formed in the tube member. The plurality of cuts formed in the tube member extend circumferentially around the longitudinal axis of the tube member with a cut length, width, pitch, and other parameters predesigned. The plurality of cuts may be vertical cuts, circumferentially extending along paths each being vertical to the longitudinal axis of the tube member. The plurality of cuts may also be helical cuts, extending along a helical path around the longitudinal axis of the tube member.

According to embodiments of the disclosure, laser is used to form the plurality of cuts or slots in the tube member. Laser beams or pulses can cut or remove materials from a thin tubular part or tube member with high precision and resolution, creating no mechanical deformation or burrs. According to embodiments of the disclosure, micron- or submicron-sized patterns and/or geometries are formed with laser pulses. The laser cutting process can be automated or configured with a computer software for efficient high-speed processing.

Various types of lasers are available in the art and can be selected for use in the method of making guidewire devices of the disclosure. According to embodiments of the disclosure, a gas-assist laser is used to cut the tube member in which a pressurized gas jet or assist gas, is utilized to blow away molten material, cools the material, and prevents it from warping or re-solidifying to improve the quality and efficiency of the cutting process.

The duration, frequency, shape, and other parameters of the laser pulses can be set or selected based on the cut dimensions, geometries, and cutting speed, etc. If the tube member is thin, a high pulse frequency and short pulse duration can be used. Pulse duration is the elapsed time between the beginning and the end of a single pulse of energy, measured in seconds. The shorter the pulse duration, the greater the effectiveness of the cut, with fewer burrs or defects, such as heat-affected zones. Ultrashort pulses ranging from tens of picoseconds to femtoseconds can be used in embodiments of the disclosure.

A stage can be used to hold and/or move the tube member during the cutting process. The stage can be controlled by a precision motor system, which can translate and/or rotate the tube member at a micron or sub-micron precision level. For example, in the cutting process the tube member can be held and/or moved by the stage while beam pulses from a laser source are aimed at and deposited on the tube member. In some embodiments, the laser source includes a chain of optics which can be controlled and/or adjusted during the cutting process while the tube member is being held and/or moved by the stage.

In an embodiment, the tube member is held at a fixed axial location. A laser source can be actuated to deposit pulses of beams on to the tube member while the tube member is being rotated or turned at the fixed axial location, forming a cut with a predetermined cut width and/or length. The cut can be a transverse cut formed in a plane normal to the longitudinal axis of the tube member, or in a plane at an angle to the plane normal to the longitudinal axis of the tube member. After the desired length of a cut (as measured by degrees) is achieved, the laser source can be turned off.

In an embodiment, the tube member is held at a first axial location. Pulses of laser beam can be deposited to the tube member while the tube member is being rotated at the first axial location. A first vertical cut is formed at the first axial location of the tube member. Then, the tube member is translated to a second axial location. Pulses of laser beam can be deposited to the tube member while the tube member is being rotated at the second axial location. A second vertical cut is formed at the second axial location of the tube member. In this manner, a plurality of vertical cuts can be formed in the tube member at a plurality of axial locations.

In an embodiment, the tube member is translated from a first axial location to a second axial location and rotated during the translation. Pulses of laser beam can be deposited to the tube member while the tube member is being translated and rotated simultaneously. In this manner, a helical cut can be formed in the tube member extending between the first axial location and the second axial location of the tube member. The laser source can be turned on and off while the tube member is being translated and rotated simultaneously to form a plurality of helical cuts.

At step 1208, the tube member is coupled to the elongate polymer liner. The polymer liner can be inserted inside the tube member and securely combined with the tube member using suitable bonding means.

At step 1210, a jacket layer can be applied to the tube member-polymer liner assembly e.g. by coating. Suitable materials for the jacket layer include but are not limited to thermoplastic elastomer (TPE) such as polyether block amide, thermoplastic polyurethane, polyethylene, nylon, or the like.

Various embodiments of an intravascular device and a method of making intravascular devices have been described with reference to figures. It should be noted that an aspect described in conjunction with a particular embodiment is not necessarily limited to that embodiment and can be practiced in any other embodiments. The figures are intended for illustration of embodiments but not for exhaustive description or limitation on the scope of the disclosure. Alternative structures, components, and materials will be readily recognized as being viable without departing from the principle of the claimed invention. Further, while some embodiments of the disclosure are described in conjunction with a catheter device, this is not intended to be limiting. For example, the tube member including a plurality of vertical and/or helical cuts may be constructed as a component for a guidewire device and other intervascular devices. As an example, a guidewire device may include an elongate core wire and a tube member described herein disposed over a distal section of the core wire.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "proximal" and its grammatically equivalent refers to a position, direction or orientation towards the user or physician's side. The term "distal" and its grammatically equivalent refers to a position, direction, or orientation away from the user or physician's side. The designations "rearward," "forward," and the like are not meant to limit the referenced component to a specific orientation. It will be appreciated that such designations refer to the orientation of the referenced component as illustrated in the Figures; the systems and devices of the disclosure can be used in any orientation suitable to the user. The term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. The order in which the method steps are performed may be changed in alternative embodiments. One or more method steps may be skipped altogether, and one or more optional steps may be included. All numeric values are provided for illustration and assumed to be modified by the term "about," whether explicitly indicated or not. The term "about" generally refers to a range of numbers that one of skill in the art would consider equivalent to the recited value e.g., having the same function or result. The term "about" may include numbers that are rounded to the nearest significant figure. The recitation of a numerical range by endpoints includes all numbers within that range.

Those skilled in the art will appreciate that various other modifications may be made. All these or other variations and modifications are contemplated by the inventors and within the scope of the invention.

What is claimed is:

1. An intravascular device comprising a tube member, the tube member comprising a distal portion and a proximal portion, wherein the distal portion of the tube member comprises a plurality of cuts circumferentially extending around a longitudinal axis of the tube member, the plurality of cuts of the distal portion of the tube member comprising a first pitch, a first cut length, a first uncut length, and a first cut width;

the proximal portion of the tube member comprises a plurality of cuts circumferentially extending around the longitudinal axis, the plurality of cuts of the proximal portion of the tube member comprising a second pitch, a second cut length, a second uncut length, and a second cut width;

the first pitch is less than the second pitch, the first cut length is greater than the second cut length, the first uncut length is less than the second uncut length, and the second cut width is less than the first cut width;

the plurality of cuts of the distal portion are helical cuts, and the plurality of cuts of the proximal portion are helical cuts;

the first cut width ranges between 0.015 mm and 0.030 mm, the second cut width ranges between 0.010 mm and 0.025 mm;

the first cut length ranges between 60 degrees and 177 degrees, the first uncut length ranges between 3 degrees and 15 degrees, the second cut length ranges between 60 degrees and 165 degrees, and the second uncut length ranges between 15 degrees and 40 degrees; and a combination of the first cut length and the first uncut length is greater than a combination of the second cut length and the second uncut length.

2. The intravascular device of claim 1, wherein the tube member further comprises a transition portion between the distal portion and the proximal portion, the transition portion of the tube member comprising a plurality of cuts circumferentially extending around the longitudinal axis of the tube member, wherein the plurality of cuts of the transition portion are helical cuts and comprises a third pitch, a third cut length, and a third uncut length.

3. The intravascular device of claim 2, wherein the third pitch of the plurality of cuts of the transition portion increases in a proximal direction.

4. The intravascular device of claim 3, wherein the third pitch increases linearly.

5. The intravascular device of claim 3, wherein the third pitch increases non-linearly.

6. The intravascular device of claim 3, wherein the third cut length and the third uncut length of the transition portion are constant.

7. The intravascular device of claim 3, wherein the third cut length decreases in the proximal direction, and the third uncut length increases in the proximal direction.

8. The intravascular device of claim 2, wherein the plurality of cuts of the transition portion comprises a third cut width less than the first cut width of the plurality cuts of the distal portion.

9. The intravascular device of claim 2, wherein the third pitch is constant, the third cut length decreases in a proximal direction, and the third uncut length increases in the proximal direction.

10. The intravascular device of claim 1, wherein the tube member further comprises a transition portion between the distal portion and the proximal portion, the transition portion of the tube member comprising a plurality of cuts circumferentially extending around the longitudinal axis of the tube member, wherein the plurality of cuts of the transition portion are vertical cuts; and the plurality of cuts of the transition portion comprises a third pitch increasing in the proximal direction, a third cut length decreasing in a proximal direction, and a third uncut length increasing in the proximal direction.

11. The intravascular device of claim 1, wherein the distal portion of the tube member extends a length of 10 cm or less from a distal end extremity of the tube member, and the proximal portion of the tube member extends from a location at 15 cm or more from the distal end extremity.

12. The intravascular device of claim 11, wherein the first pitch of the plurality of cuts of the distal portion is in a range between 0.03 mm and 0.30 mm, and the second pitch of the plurality of cuts of the proximal portion is in a range between 0.10 mm and 1.00 mm.

13. The intravascular device of claim 1, wherein a combination of the first cut length and the first uncut length is between 75 and 180 degrees, and a combination of the second cut length and the second uncut length is between 75 and 180 degrees.

14. The intravascular device of claim 1, further comprising an elongate inner liner having a lumen, wherein the tube member encompasses at least a distal portion of the elongate inner liner.

15. The intravascular device of claim 1, further comprising an elongate core wire, wherein the tube member encompasses at least a distal portion of the elongate core wire.

16. The intravascular device of claim 1, wherein the first cut width ranges between 0.015 mm and 0.025 mm, the second cut width ranges between 0.010 mm and 0.020 mm.

* * * * *